United States Patent [19]

Silvestrini et al.

[11] Patent Number: 4,610,688

[45] Date of Patent: Sep. 9, 1986

[54] TRIAXIALLY-BRAIDED FABRIC PROSTHESIS

[75] Inventors: Thomas A. Silvestrini, East Lyme; Joseph E. Laptewicz, Jr., Groton, both of Conn.

[73] Assignee: Pfizer Hospital Products Group, Inc., New York, N.Y.

[21] Appl. No.: 481,612

[22] Filed: Apr. 4, 1983

[51] Int. Cl.$^4$ ............................. A61F 2/06; A61F 2/24
[52] U.S. Cl. ............................................. 623/1; 623/2; 623/12; 128/92 C
[58] Field of Search ............................. 3/1, 1.4, 1.5; 128/92 C, 335

[56] References Cited

U.S. PATENT DOCUMENTS

| | | | |
|---|---|---|---|
| 3,176,316 | 4/1965 | Bodell | 3/1 |
| 3,431,814 | 3/1969 | Boehm | 87/2 |
| 3,613,120 | 10/1971 | McFarland, Jr. | 3/1 |
| 4,127,902 | 12/1978 | Homsy | 3/1 |
| 4,149,277 | 4/1979 | Bokros | 3/1 |
| 4,191,218 | 3/1980 | Clark et al. | 139/383 R |
| 4,192,020 | 3/1980 | Davis et al. | 3/1.5 |
| 4,209,859 | 7/1980 | Hoffman | 3/1 |
| 4,246,660 | 1/1981 | Wevers | 3/1 |
| 4,255,820 | 3/1981 | Rothermel et al. | 3/1 |
| 4,297,749 | 11/1981 | Davis et al. | 3/1.5 |
| 4,301,551 | 11/1981 | Dore et al. | 3/1 |
| 4,329,743 | 5/1982 | Alexander et al. | 3/1 |
| 4,340,091 | 7/1982 | Skelton et al. | 139/383 R |
| 4,345,339 | 8/1982 | Muller et al. | 3/1 |
| 4,371,415 | 2/1983 | Tanaka | 156/433 |
| 4,380,483 | 4/1983 | Kliger | 156/169 |
| 4,384,022 | 5/1983 | Fowler | 428/296 |
| 4,416,028 | 11/1983 | Eriksson et al. | 3/1.4 |
| 4,467,478 | 8/1984 | Jurgutis | 3/1 |
| 4,469,101 | 9/1984 | Coleman et al. | 128/334 R |

FOREIGN PATENT DOCUMENTS 51954 5/1982 European Pat. Off. .
67929 12/1982 European Pat. Off. .
82/01647 5/1982 PCT Int'l Appl. .

OTHER PUBLICATIONS

New England Butt Co., undated technical brochure.
James, S. L.; "Biomechanics of Knee Ligament Reconstruction"; Clin. Ortho. & Rel. Res., No. 146; pp. 90-101 (Jan.-Feb. 1980).
"Triaxial Fabrics for Rigid Composites are Seen Advancing State of the Art"; FRL Newsletter; vol. IV; No. 1; p. 3 (Fall 1976).
Fitzgerald, E. E.; "Mechanical Behavior of Bicomponent Braids as Potential Surgical Implants"; Master of Science Thesis; Cornell University; Aug. 1979.

Primary Examiner—Richard J. Apley
Assistant Examiner—David J. Isabella
Attorney, Agent, or Firm—Charles J. Knuth; Peter C. Richardson; Lawrence C. Akers

[57] ABSTRACT

A novel prosthesis for use in repairing or replacing soft tissue is disclosed, which comprises a triaxially-braided fabric element having interwoven first, second and third sets of fibers, with the fibers of the second and third sets being oriented at substantially the same acute braiding angle with respect to the fibers of the first set. An elongated ligament prosthesis exhibiting the desired properties of high strength and high elasticity may be prepared by selecting high elasticity fibers for the first set, orienting said first set of fibers in the longitudinal direction of the prosthesis and selecting fibers having high yield strength and high Young's modulus for the second and third sets. A tubular prosthesis in which high elasticity fibers are oriented in the longitudinal direction is highly suitable for use as a vascular prosthesis. A prosthesis of the invention may also be manufactured in the form of a prosthetic heart valve leaflet.

14 Claims, 6 Drawing Figures

TRIAXIALLY-BRAIDED FABRIC PROSTHESIS

BACKGROUND OF THE INVENTION

The natural ligaments are elongated bundles of collagenous soft tissue that serve, among other things, to hold the component bones of joints together. The surgical treatment of diseased or damaged ligaments, e.g. the anterior cruciate ligament, has been severely hampered by the unavailability of a suitable, generally accepted ligament prosthesis. The desired characteristics for a ligament prosthesis include appropriate size and shape, biological compatibility, capability of being readily attached by the surgeon to the body of the patient, high fatigue resistance and mechanical behavior approximating that of the ligamentous tissue sought to be repaired or replaced.

The latter desired characteristic is particularly important. Natural ligaments are both strong and highly elastic, which qualities are generally not found together in a single material. Thus, for example, the anterior cruciate ligament of normal adult humans exhibits a yield point in tension of about 50 kg. at a reversible elongation of about 28%, and a break point of about 60 kg. (Typical adult human tendons are stronger and less elastic.) A number of ligament and/or tendon prostheses are known in which the load bearing body portion is fabricated essentially of a single synthetic material (see, e.g., U.S. Pat. Nos. 3,176,316; 3,613,120; 4,127,902; 4,149,277; 4,209,859; 4,255,820; 4,329,743 and 4,345,339; U.K. Pat. No. 1,602,834 and European Published Patent Appln. 51,954). These monocomponent devices generally possess insufficient longitudinal elasticity and some also exhibit inadequate longitudinal break strength. As a result of their insufficient elasticity, this type of prosthesis must be forced into the region of plastic deformation to achieve the longitudinal elongation desired for normal anatomical function, e.g. flexion of a joint, which of course permanently impairs the mechanical function of the prosthesis.

Recently, ligament prostheses have been disclosed in U.S. Pat. Nos. 4,246,660 and 4,301,551 in which the load bearing body portion is a bicomponent structure comprised of one material that imparts strength to the prosthesis and another material that imparts elasticity. The use of these prostheses alleviates the disadvantages described above for the monocomponent type of prosthesis. However, the prostheses disclosed in the '660 and '551 Patents are complex in construction and their methods of attachment to the body of the patient involve rather complicated surgical procedures.

A recent thesis (Elizabeth E. Fitzgerald, "Mechanical Behavior of Bicomponent Braids as Potential Surgical Implants", Master of Science Thesis, Cornell University, August 1979) has disclosed the use of a braided bicomponent tube as a ligament prosthesis. In this prosthesis two interwoven sets of polymeric fibers, one of a strong material and the other of an elastic material, are helically-disposed in the wall of the tube and oriented at a fixed angle with respect to one another. Each set of fibers is oriented at the same acute angle with respect to the longitudinal direction of the tube. The prosthesis may additionally comprise a monocomponent polymeric filament core.

The prosthesis disclosed in the Fitzgerald thesis has certain inherent disadvantages. First, since the fibers in the two helically-disposed interwoven sets are not identical, the prosthesis is not balanced and will tend to twist during longitudinal elongation. Second, since the set of helically-disposed elastic fibers is angulated with respect to the longitudinal direction of the prosthesis, only a minor amount of the work performed in elongating the prosthesis longitudinally is converted to elastic energy stored in the extended set of elastic fibers. Undesirably large portions of said work are converted to elastic energy stored in the other set of strong fibers or dissipated as friction in the extending trellis-like bicomponent braided structure.

SUMMARY OF THE INVENTION

It is an object of the present invention to provide a ligament prosthesis of simple construction that exhibits a yield strength in tension and a longitudinal elasticity that are at least comparable to that of a human ligament and a resistance to longitudinal elastic deformation in tension that approximates that of a human ligament.

Is is another object of the invention to provide a balanced braided prosthesis of such construction that its longitudinal load-strain behavior can be readily "fine-tuned", while maintaining balance, to suit particular applications by changing component materials and/or braiding variables.

These and other objects of the invention are achieved with a novel prosthesis for use in repairing or replacing soft tissue comprising a triaxially-braided fabric element containing interwoven first, second and third sets of fibers, with the fibers of said first set being oriented in substantially the same direction, the fibers of said second and third sets being oriented at substantially the same acute braiding angle with respect to the fibers of the first set, and the fibers of one of said three sets having greater elasticity than the fibers of one or both of the other two of said three sets. One important embodiment of the novel prosthesis of the invention is a prosthesis adapted for use in repairing or replacing ligament or tendon tissue, in which embodiment the prosthesis has first and second opposed end portions adapted to be attached with the prosthesis in tension to the body of a patient, with said two end portions defining between them the longitudinal direction of the prosthesis, the fibers of the first set are oriented in substantially said longitudinal direction of the prosthesis the fibers of the first set have greater elasticity than the fibers of both of said second and third sets, and the fibers of the second and third sets have greater yield strength and Young's modulus than the fibers of the first set. By increasing (or decreasing) the braiding angle with other variables fixed, the resistance of this ligament or tendon prosthesis to deformation under longitudinal loading may be decreased (or increased). Preferably, the fibers of the second set in the ligament or tendon prosthesis are identical with the fibers of the third set. In a preferred design for a ligament or tendon prosthesis of the invention, the fabric element of said prosthesis has the shape of a cylindrical tube, the fibers of the first set are oriented in the longitudinal direction of said tube and the fibers of the second and third sets are helically-disposed in the wall of said tube.

The broad conception of the present invention comprises numerous other embodiments in addition to the ligament or tendon prosthesis discussed in the preceding paragraph, such as a vascular graft prosthesis in which the woven fabric element has the shape of a cylindrical tube, the fibers of the first set are oriented in the longitudinal direction of said tube, the fibers of the second and third sets are helically-disposed in the wall of said tube, and the fibers of the first set have greater elasticity than the fibers of both of said second and third sets. The present invention also includes a prosthetic heart valve leaflet in the form of a sheet in which the fibers of the first set are oriented in the circumferential direction of the valve and have greater yield strength and Young's modulus than the fibers of the second and third sets, and the fibers of the second and third sets have greater elasticity than the fibers of the first set.

As used herein, the terms "yield strength" and "yield stress" are synonymous and refer to the tensile stress (in units of force per unit cross-sectional area) at which significant (i.e. greater than 0.2% of initial length) plastic deformation of a naturally-occurring or synthetic object occurs. The term "Young's modulus" refers to the ratio of the tensile stress placed on an object in elastic deformation to the resulting longitudinal strain. The term "elasticity" refers to the amount of recoverable elongation of a tensioned article, i.e. the percent elongation (expressed as a percentage of initial length) at the yield stress defined above. Note that as a matter of definition a "highly elastic" material (i.e. a material exhibiting a high elasticity) may be either highly resistant to elastic deformation (high Young's modulus) or not (low Young's modulus).

DETAILED DESCRIPTION OF THE INVENTION

The invention will be described in detail with reference to a preferred embodiment thereof, which is a ligament prosthesis. Reference to this embodiment does not limit the scope of the invention, which is limited only by the scope of the claims.

Figure 1:
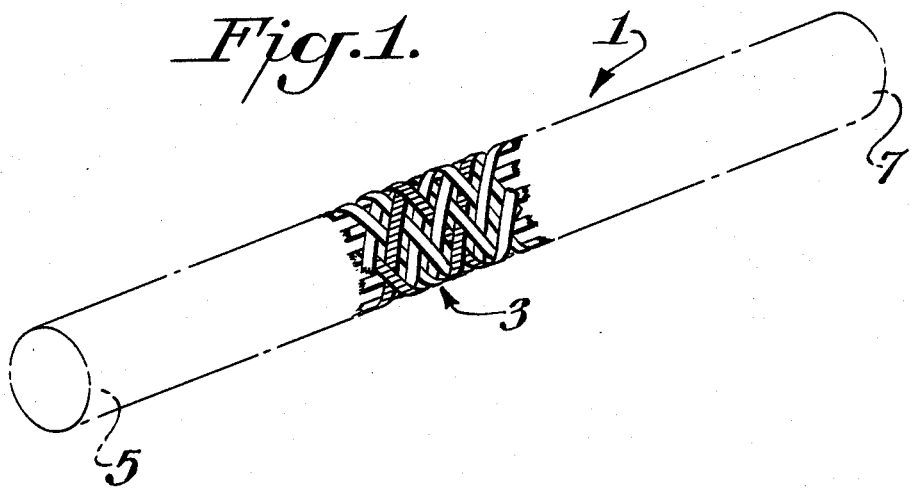
FIG. 1 is a perspective view of a ligament or vascular prosthesis of the invention.

A ligament prosthesis 1 of the invention, which consists of a triaxially-braided fabric element 3 having opposed end portions 5 and 7 defining between them the longitudinal direction of the prosthesis, is shown in FIG. 1. In the embodiment shown in FIG. 1, prosthesis 1 and fabric element 3 are coincident, but (as will be explained below) this is not always necessarily so. Fabric element 3 in FIG. 1 has the form of a seamless cylindrical tube; although only a portion of the braided structure of fabric element 3 is shown in FIG. 1, it is to be understood that said braided structure actually extends along the entire length of element 3 from end portion 5 to end portion 7.

Figure 2:
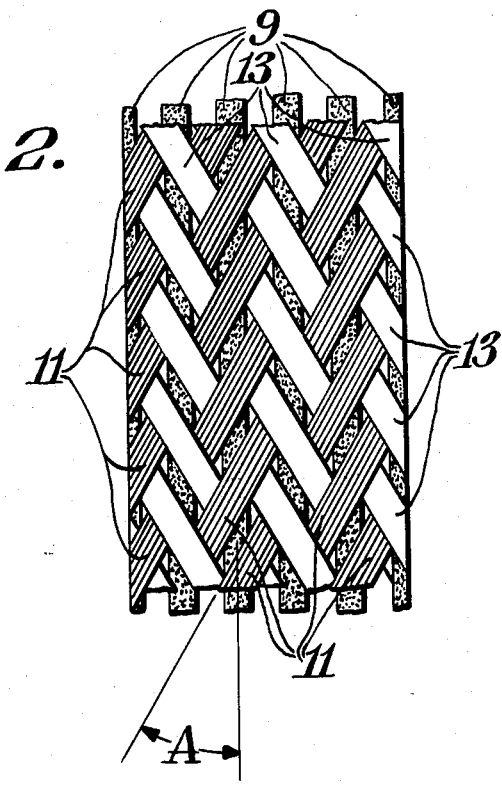
FIG. 2 is an enlarged view of the braided structure of the prosthesis of FIG. 1.

An enlarged view of the braided structure of fabric element 3 is shown in FIG. 2, in which figure the vertical direction is the longitudinal direction of the prosthesis. Fabric element 3 contains interwoven first, second and third sets 9, 11 and 13, respectively, of fibers. The fibers of first set 9 are straight and oriented in substantially the same warp direction, i.e. the longitudinal direction of the prosthesis. The weft fibers of second and third sets 11 and 13 are helically-disposed in the wall of tubular fabric element 3 (see FIG. 1) and are oriented at substantially the same acute braiding angle A (see FIG. 2) with respect to the fibers of first set 9. Each fiber of set 9 is held between the fibers of sets 11 and 13. The weft fibers of sets 11 and 13 are preferably disposed in a two-up and two-down manner with respect to one another and in a one-up and one-down manner with respect to the fibers of set 9. Other braiding patterns may alternatively be employed, such as the disposition of the fibers of sets 11 and 13 with respect to one another in a one-up and one-down or two-up and one-down manner. In FIG. 2, braiding angle A is about 30°. Preferably, all of the fibers in fabric element 3 have circular cross-sections of about the same diameter. If desired, various fibers in one or both of the sets 11 and 13 may be dyed to provide a means to indicate the degree of tension and elongation being experienced by the prosthesis. For example, as illustrated in FIG. 1, two fibers in each helical set may be dyed. As the prosthesis is tensioned, the spacing between the dyed fibers increases according to a predetermined relationship between tensile load and strain for the prosthesis. Thus, if implantation in a pretensioned state is desirable, the surgeon may be provided with a linear gauge showing the desired dyed fiber spacing at a desired state of pretension for the prosthesis.

Triaxially-braided fabrics such as the one depicted in FIG. 2 and the methods of manufacturing them in different configurations (flat sheets, tubes, patches, strips, etc.) are well known to those skilled in the art of manufacturing braided polymeric articles (see for example U.S. Pat. Nos. 4,191,218; 4,192,020 and 4,297,749). Braiding angles of from about 10° to about 80° are attainable. A significant advantage of using a triaxially-braided fabric element such as element 3 as a ligament prosthesis is that the element can be readily implanted in a tensioned state by attaching its two end portions, e.g. 5 and 7, to the body of a patient (for example to the two bones making up a joint or to the two free ends of a severed natural ligament) by means of simple stapling or suturing techniques. Of course, if desired, a ligament or tendon prosthesis of the invention may include, in addition to a triaxially-braided fabric element, distinct means (for example those disclosed in U.S. Pat. No. 4,246,660) attached to the end portions of the fabric element for securing the prosthesis to the body of the patient.

Figure 3:
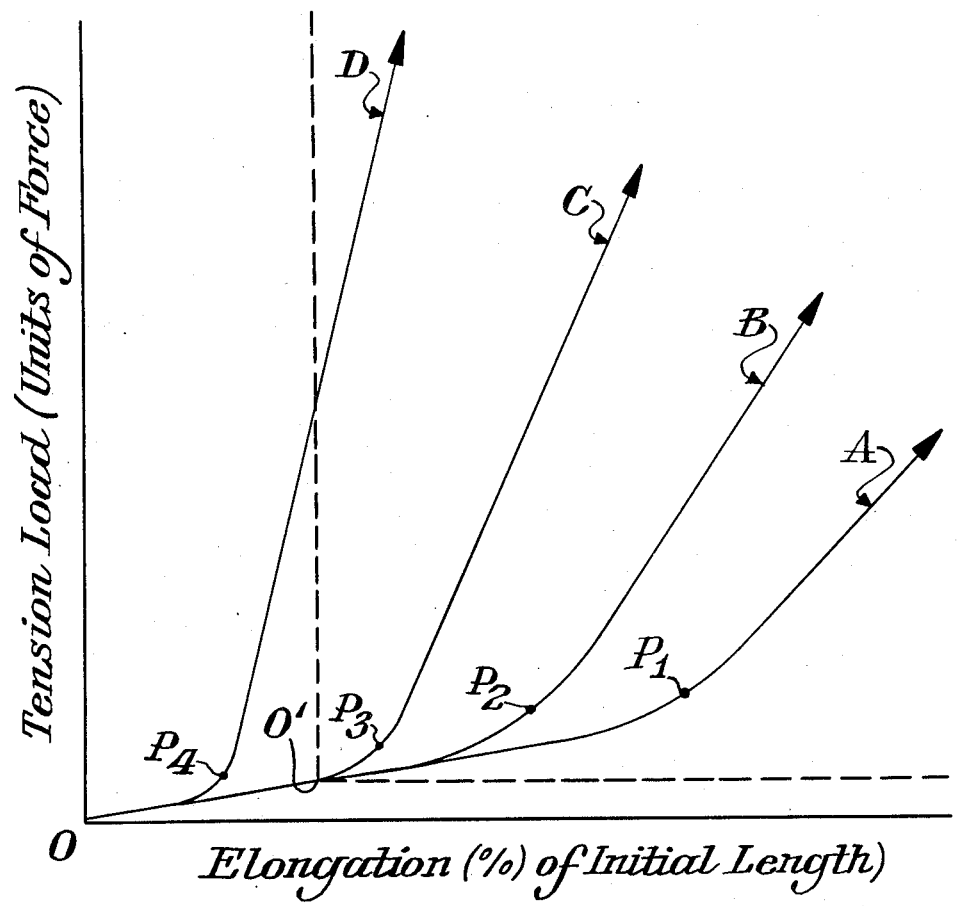
FIG. 3 is a schematic representation of the load-strain behavior of the prosthesis of FIG. 1, showing the effect of braiding angle.

In the ligament prosthesis 1 depicted in FIGS. 1 and 2 the longitudinally-oriented straight inlaid fibers of set 9 have greater elasticity than the fibers of helically-disposed sets 11 and 13, while the fibers of sets 11 and 13 have greater yield strength and Young's modulus than the fibers of set 9. As a result, the set 9 fibers provide the ligament prosthesis with the desired elasticity, while the set 11 and set 13 fibers provide the desired strength and resistance to longitudinal tensile deformation of the composite prosthetic article. The applied axial tensile load—% axial elongation curve for prosthesis 1 (not pretensioned) is shown schematically as curve C in FIG. 3. Initially, the slope of the load vs. elongation curve is quite low as the load is borne primarily by the elastic fibers of set 9. As elongation increases, however, the helically-disposed fibers of sets 11 and 13 become more aligned with the direction of elongation. As a result the slope of the load vs. elongation curve for the prosthesis increases sharply in the vicinity of point $P_3$.

Eventually the yield point of the prosthesis is reached, which is essentially equal to the yield point of the thyleneterephthalate. Other alternative combinations of fibers are listed (non-exclusively) below:

| Set 9 | Set 11 | Set 13 |
|---|---|---|
| polyurethane polymer | nylon | nylon |
| polyurethane polymer | aromatic polyamide polymer | aromatic polyamide polymer |
| polyurethane polymer | isotactic polypropylene | isotactic polypropylene |
| polyurethane polymer | polyglycolic acid | polyglycolic acid |
| polyurethane polymer | polylactic acid | polylactic acid |
| polyurethane polymer | polyethyleneterephthalate | polyethyleneterephthalate |
| silicone elastomer | polyethyleneterephthalate | polyethyleneterephthalate |
| silicone elastomer | nylon | nylon |
| silicone elastomer | aromatic polyamide polymer | aromatic polyamide polymer |
| silicone elastomer | isotactic polypropylene | isotactic polypropylene |
| silicone elastomer | polyglycolic acid | polyglycolic acid |
| polyester/polyether block copolymer | polyethyleneterephthalate | nylon |
| polyester/polyether block copolymer | nylon | nylon |
| polyester/polyether block copolymer | aromatic polyamide polymer | aromatic polyamide polymer |
| spandex-type polyurethane/polyether block copolymer | polyethyleneterephthalate | polyethyleneterephthalate |
| spandex-type polyurethane/polyether block copolymer | nylon | nylon |
| spandex-type polyurethane/polyether block copolymer | aromatic polyamide polymer | aromatic polyamide polymer |
| spandex-type polyurethane/polyether block copolymer | polyglycolic acid | polyglycolic acid |
| spandex-type polyurethane/polyether block copolymer | nylon | nylon |
| spandex-type polyurethane/polyether block copolymer | aromatic polyamide polymer | aromatic polyamide polymer |
| spandex-type polyurethane/polyether block copolymer | polyethyleneterephthalate | polyethyleneterephthalate |
| hard elastic polypropylene | polyethyleneterephthalate | polyethyleneterephthalate | woven assembly of the fibers of sets 11 and 13. An important characteristic of prosthesis 1 is the orientation of the elastic fibers of set 9 in the longitudinal direction of the prosthesis, which permits the storage of a large amount of elastic energy in the elongating fibers of this set. Significant additional elastic energy is stored in the compression of the fibers of set 9 by the fibers of sets 11 and 13 during elongation of the prosthesis. Only a small amount of applied work is dissipated as friction.

The fibers of the interwoven three sets in a prosthesis of the invention are preferably made of synthetic polymeric materials, although naturally-occurring (e.g. silk) and inorganic (e.g. stainless steel) fibers may also be used. If desired, biologically resorbable fibers may be employed. It is usually preferred that the fibers of the second and third sets be identical and equal in number. The elastic fibers of the first set in a ligament and/or tendon prosthesis of the invention such as prosthesis 1 may, for example, be selected from the group consisting of polyurethane polymers, silicone elastomers, polyester/polyether block copolymers, spandex-type polyurethane/polyether block copolymers, spandex-type polyurethane/polyester block copolymers, and hard elastic polypropylene. The strong and stiff fibers of the second and third sets in such a prosthesis may, for example, be selected from the group consisting of polyethyleneterephthalate, nylon, aromatic polyamide polymers such as Kevlar (E. I. du Pont de Nemours & Co.; Wilmington, Del.), isotactic polypropylene, polyglycolic acid and polylactic acid. Other suitable materials are readily apparent to those skilled in the art of polymer chemistry. As just one specific example, the fibers of first set 9 of prosthesis 1 may be made of a polyester/polyether block copolymer such as Hytrel (DuPont) and the fibers of sets 11 and 13 of polye- Aside from the materials selected for the three sets of fibers in a prosthesis of the invention and the overall configuration and dimensions of the prosthesis, the resulting mechanical properties of the prosthesis, e.g. prosthesis 1 in FIGS. 1 and 2, are also materially affected by the various braiding variables, e.g. the fiber diameters, braiding angle, braiding tension, density of windings, number ratio of fibers in the three sets and braiding pattern. Of considerable importance is the braiding angle, illustrated as angle A in FIG. 2. As is shown schematically in FIG. 3, the resistance of prosthesis 1 to deformation under axial loading in tension increases as the braiding angle is decreased (curve A to curve D). Furthermore, the percent elongation of prosthesis 1 (as a percentage of initial length) at which significant plastic deformation or breakage of the prosthesis commences decreases as the braiding angle is decreased. Thus it can be seen that, with all other variables fixed, the load-strain behavior of prosthesis 1 can be adjusted to approximate that of a natural ligament or tendon sought to be repaired or replaced by varying the braiding angle. Additionally, with all other variables fixed and the fibers of the second and third sets identical and equal in number, the load-strain behavior of prosthesis 1 can be substantially adjusted by varying the numerical ratio of fibers in the three sets, e.g. from 1 (longitudinal):1 (helical):1 (helical) to 0.5 (longitudinal):1 (helical):1 (helical), while maintaining a balanced prosthesis. The above-indicated change in number ratio would render the prosthesis more resistant to elongation under axial loading in tension.

In addition to mechanical properties, the wall porosity of a prosthesis of the invention may be varied in a predictable manner by altering the braiding variables, particularly the fiber diameters, braiding tension and density of windings. A relatively high porosity permits, if desired, substantial tissue ingrowth into the wall of the fabric element of the prosthesis, while a relatively low porosity minimizes such ingrowth if it is not desired. Generally, tissue ingrowth is desired in a permanent prosthesis but not in a temporary one.

The triaxially-braided fabric element of a ligament and/or tendon prosthesis of the invention may have other shapes than the cylindrical tube shown in FIG. 1. Thus, the fabric element may have the shape of a flattened cylindrical tube. As another example, the fabric element of a ligament and/or tendon prosthesis may have the shape of a flat elongated strip, in which the straight, longitudinally-oriented elastic fibers of the first set are disposed in essentially a single plane and each of the fibers of the second and third sets traverses said plane in a zig-zag manner (as depicted in FIG. 9 of U.S. Pat. No. 4,191,218) while maintaining a constant braiding angle.

The present invention is by no means limited to ligament and/or tendon prostheses, but includes prostheses for other soft tissue structures as well (e.g., blood vessels). Thus, for example, a vascular prosthesis of the invention such as an aortic graft prosthesis may have the same shape (but typically a different diameter) as the prosthesis 1 shown in FIG. 1. In such a vascular prosthesis, the fibers of sets 9, 11 and 13 are all elastic, with the straight fibers of longitudinally-oriented set 9 being more or less elastic, preferably more elastic, than the fibers of both of the other two sets. Accordingly, a tubular vascular prosthesis may be provided with high elasticity in the longitudinal direction as well as substantial elasticity in the radial direction to accomodate the pulsing flow of blood in vivo. If desired, such a tubular vascular prosthesis may include an impermeable elastic internal coating or tubular insert.

Figure 6:
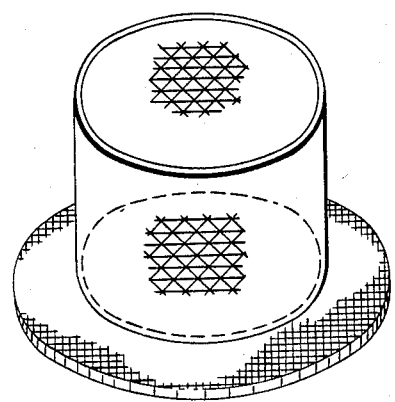
FIG. 6 is an exploded view of a heart valve prosthesis of the invention, in which only a portion of the braided structure of each valve leaflet is shown.

Additionally, a heart valve prosthesis of the invention (see FIG. 6) may comprise a frame having a generally circular base defining the circumferential direction of the prosthesis and a plurality of spaced, generally parallel legs extending from the base; and a plurality of triaxially-braided fabric elements having the form of sheets and attached by conventional means to the frame in such a manner that they function as heart valve leaflets during the operation of the valve. Preferably, in each of said fabric elements, the fibers of the first set are oriented in the circumferential direction of the valve when the valve is in the open position, the fibers of the second and third sets traverse the first set of fibers in a zig-zag manner (as depicted in FIG. 9 of U.S. Pat. No. 4,191,218), the fibers of the first set have greater yield strength and Young's modulus than the fibers of the second and third sets, and the fibers of the second and third sets have greater elasticity than the fibers of the first set. Accordingly, an artificial heart valve prosthesis leaflet is provided that is capable of substantial elastic stretching in directions generally orthogonal to the circular base of the frame of the heart valve prosthesis.

The use of prostheses of the invention to repair or replace soft tissue requires only simple surgical procedures. After diseased or damaged soft tissue has been removed, the ends of a prosthesis of the invention may be readily attached to bone (e.g. with conventional bone staples) or to soft tissue (e.g. by suturing). Prostheses of the present invention may be cut to a desired length without unravelling. If desired, two tubular prostheses of the invention may be readily anastomosed in an end-to-end fashion. To prevent fraying of the triaxially-braided fabric element the free ends of the fibers at the edge of the element may be fused together, e.g. by ultrasonic welding or by dipping the edge of the element in a suitable coating material. A ligament and/or tendon prosthesis of the invention may be preconditioned before use by applying and releasing an axial tensile load (e.g. 60 lbs.) a number of times. In the case of an anterior cruciate ligament prosthesis, the prosthesis is preferably implanted in a longitudinally pretensioned state. Then, the observed load-strain behavior of the implanted prosthesis is that relative to an origin such as the origin O′ on curve C defined by the dotted abscissa and ordinate in FIG. 3.

Conventional techniques (see for example the article by James, S. L., "Biomechanics of Knee Ligament Reconstruction", Clin. Orthoped. and Related Res., No. 146, pp. 90–101 (Jan.-Feb. 1980)) may be employed in attaching a ligament prosthesis of the invention to the patient's body. Preferably, a short end length of the prosthesis (e.g. prosthesis 1) is folded over once (i.e. lap folded) and the attachment to the body effected at this doubled region. The surgical joining of a severed natural tendon may be facilitated by slipping a tubular prosthesis of the invention over the free end of one portion of the severed tendon, surgically joining the two portions of the tendon and then attaching the prosthesis to the two respective portions of the severed tendon. The prosthesis serves to support the healing tendon and can be removed after the healing has been accomplished.

By appropriate selection of braiding and other variables the mechanical properties of various natural human ligaments and tendons can be closely approximated by a prosthesis of the present invention. Often, in order to make such a match, it is desired that the prosthesis exhibit a tensile break point of at least about 75 kg. and, after initial pretension, an overall load modulus of from about 200 kg./(unit of strain based on pretensioned length) to about 600 kg./(unit of strain based on pretensioned length) over a range of substantially recoverable tensile elongation beginning at the pretensioned state and extending over a strain equal to at least about 25 percent of the initial pretensioned length of the prosthesis. Two examples of prosthesis 1 having these desired properties are set forth below. These examples are not to be construed as limiting the invention.

EXAMPLE 1

Set 9—Longitudinal fibers—48 ends—Hytrel Type 5556 polyester/polyether block copolymer monofilament (E. I. du Pont de Nemours & Co.; Wilmington, Del.)—220 denier Set 11—Helical fibers—46 ends of 220 denier Dacron Type 52 polyethyleneterephthalate twisted multifilament (Du Pont) and 2 ends of 250 denier Dacron Type 55 polyethyleneterephthalate twisted multifilament (Du Pont) dyed with D & C green dye No. 6

Set 13—Helical fibers—same as set 11 Prosthesis configuration—flattened circular cylindrical tube 1.5 inches in length—21 mm. circumference Braiding angle—45°

Braiding pattern of sets 11 and 13 with respect to one another—2-up and 2-down

Density of windings of sets 11 and 13 -35 picks per inch

Figures 4, 5:
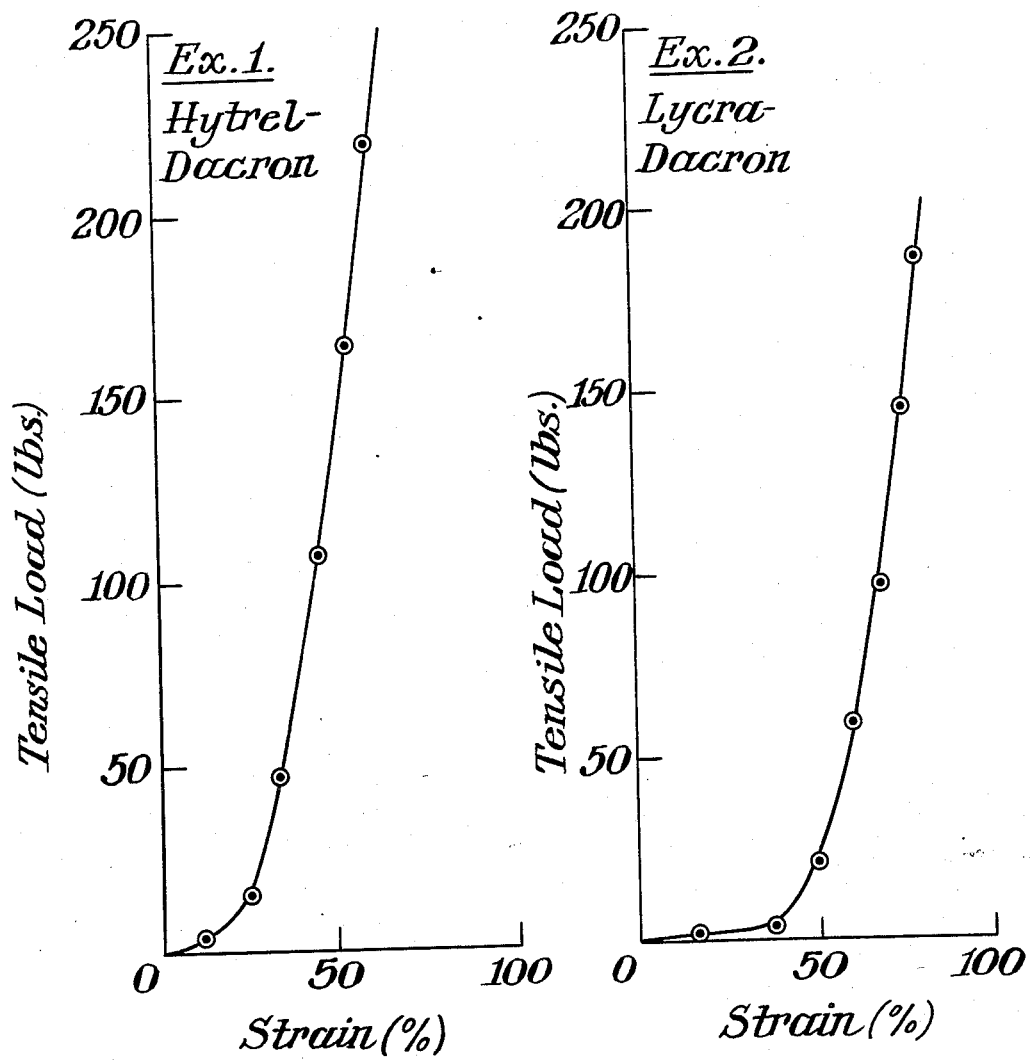
FIGS. 4 and 5 depict the load-strain behavior of particular ligament prostheses of the invention.

Braiding tension—50 to 55 g. on longitudinal fibers, 3 oz. braider carrier springs on helical fibers The above-described prosthesis exhibited the load-strain behavior shown in FIG. 4 (the origin is drawn with reference to the untensioned state). The prosthesis exhibits a tensile break point of 250 lbs.=113 kg. If the prosthesis is pretensioned to, for example, 10 lbs. tension (20% strain), it will exhibit an overall load modulus over a range of 37% of the pretensioned length of the prosthesis (equivalent to 44% of untensioned length) of (250-10) lbs./(0.37 unit of strain)=295 kg./(unit of strain). Above 20 lbs. load, the prosthesis will exhibit a substantially constant load modulus of (250-20)lbs./(0.31 unit of strain)=340 kg./(unit of strain). No distinct yield point is observed to breakage.

EXAMPLE 2

Set 9—Longitudinal fibers—48 ends—Lycra Type 127 spandex-type polyurethane/polyether block copolymer coalesced multifilament (du Pont) —280 denier
Sets 11 and 13—Helical fibers—same as in Example 1
Prosthesis configuration—same as in Example 1 except that circumference of tube is 19 mm.
Braiding angle—48°
Braiding pattern of sets 11 and 13 with respect to one another—2-up and 2-down
Density of windings of sets 11 and 13 -42 picks per inch
Braiding tension—20 to 25 g. on longitudinal fibers, 3 oz. braider carrier springs on helical fibers The above-described prosthesis exhibited the load-strain behavior shown in FIG. 5 (the origin is drawn with reference to the untensioned state). The prosthesis exhibits a tensile break point of 202 lbs.=92 kg. If the prosthesis is pretensioned to, for example, 7 lbs. tension (40% strain), it will exhibit an overall load modulus over a range of 29% of the pretensioned length of the prosthesis (equivalent to 40% of untensioned length) of (202-7) lbs./(0.29 unit of strain)=305 kg./(unit of strain). Above 20 lbs. load the prosthesis will exhibit a substantially constant load modulus of (202-20) lbs./(0.23 unit of strain)=360 kg./(unit of strain). No distinct yield point is observed prior to breakage.

We claim:

1. A prosthesis for use in repairing or replacing ligament or tendon tissue, said prosthesis having first and second opposed end portions adapted to be attached with the prosthesis in tension to the body of a patient, with said two end portions defining between them the longitudinal direction of the prosthesis, and said prosthesis comprising a triaxially-braided fabric element containing interwoven first, second and third sets of fibers, with the fibers of said first set being elastic and oriented in substantially said longitudinal direction of the prosthesis, the fibers of said second and third sets being oriented at substantially the same acute braiding angle with respect to the fibers of said first set, the fibers of said first set having greater elasticity than the fibers of both of said second and third sets, the fibers of said second and third sets having greater yield strength and Young's modulus than the fibers of said first set, and said prosthesis exhibiting a tensile break point of at least about 75 kg.

2. A prosthesis of claim 1 wherein said braiding angle is from about 10° to about 80°, whereby the resistance of said prosthesis to longitudinal deformation under longitudinal tensile loading decreases as said braiding angle is increased.

3. A prosthesis of claim 2 wherein the fibers of said second set are identical with the fibers of said third set.

4. A prosthesis of claim 3 wherein the fibers of said first set are made of a polyester/polyether block copolymer and the fibers of said second and third sets are made of polyethyleneterephthalate.

5. A prosthesis of claim 3 wherein the fibers of said first set are made of a polyurethane/polyether block copolymer and the fibers of said second and third sets are made of polyethyleneterephthalate.

6. A prosthesis of claim 3 wherein the fibers of said first set are made of a polyurethane/polyester block copolymer and the fibers of said second and third sets are made of polyethyleneterephthalate.

7. A prosthesis of claim 1 wherein said element has the shape of a cylindrical tube, the fibers of said first set are oriented in the longitudinal direction of said tube and the fibers of said second and third sets are helically-disposed in the wall of said tube.

8. A prosthesis of claim 1 wherein said element has the shape of a flat elongated strip, the fibers of said first set are oriented in the longitudinal direction of said strip in essentially a single plane and the fibers of said second and third sets traverse said plane in a zig-zag manner.

9. A prosthesis of claim 1 wherein said fabric element includes means to visually indicate the degree of extension of said prosthesis in tension.

10. A prosthesis of claim 3 wherein said triaxially-braided fabric element contains interwoven first, second and third sets of synthetic polymeric fibers, and said prosthesis exhibits, after initial pretension, an overall load modulus of from about 200 kg./unit of strain) to about 600 kg./(unit of strain) over a range of substantially recoverable tensile elongation amounting to at least about 25 percent of the initial pretensioned length of the prosthesis.

11. A vascular prosthesis comprising a triaxially-braided fabric element containing interwoven first, second and third sets of fibers, with said element having the shape of a cylindrical tube, the fibers of said first set being elastic and oriented in the longitudinal direction of said tube, the fibers of said second and third sets being elastic and helically-disposed in the wall of said tube at substantially the same acute braiding angle with respect to the fibers of said first set, and the fibers of said first set having greater elasticity than the fibers of both of said second and third sets.

12. A prosthesis of claim 11 wherein said braiding angle is from about 10° to about 80°.

13. A heart valve prosthesis comprising:
a frame having a generally circular base defining the circumferential direction of the prosthesis and a plurality of spaced, generally parallel legs extending from said base; and
a plurality of triaxially-braided fabric elements having the form of sheets and attached to said frame in such a manner that they function as heart valve leaflets during the operation of the valve, with each of said fabric elements containing interwoven first, second and third sets of fibers, with the fibers of said first set being oriented in substantially the same direction and the fibers of said second and third sets being oriented at substantially the same acute braiding angle with respect to the fibers of said first set, and wherein, in each of said fabric elements, the fibers of said first set are oriented in the circumferential direction of said valve when said valve is in the open position, the fibers of said second and third sets traverse said first set of fibers in a zig-zag manner, the fibers of said first set have greater yield strength and Young's modulus than the fibers of both of said second and third sets, and the fibers of said second and third sets have greater elasticity than the fibers of said first set.

14. A prosthesis of claim 13 wherein said braiding angle is from about 10° to about 80°.

* * * * *